(12) United States Patent
Bulkes et al.

(10) Patent No.: US 6,389,097 B1
(45) Date of Patent: May 14, 2002

(54) MULTI-PLATE VOLUMETRIC CT SCANNER GAP COMPENSATION METHOD AND APPARATUS

(75) Inventors: Cherik Bulkes, Sussex; Jiang Hsieh, Brookfield; John M. Sabol, Sussex, all of WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/751,103

(22) Filed: Dec. 28, 2000

(51) Int. Cl.⁷ .................................................. A61B 6/03
(52) U.S. Cl. ........................................... 378/19; 378/15
(58) Field of Search .............................. 378/4, 15, 19, 378/901

(56) References Cited

U.S. PATENT DOCUMENTS 6,046,454 A * 4/2000 Lingren et al. ........ 250/370.01
6,194,726 B1 * 2/2001 Pi et al. ................... 250/363.1
6,226,350 B1 * 5/2001 Hsieh ......................... 378/98
6,233,308 B1 * 5/2001 Hsieh ......................... 378/62

\* cited by examiner

*Primary Examiner*—David V. Bruce
(74) *Attorney, Agent, or Firm*—Quarles & Brady, LLP; Christian G. Cabou

(57) ABSTRACT

A method and apparatus for configuring a large CT detector using a plurality of smaller X-ray type detector panels wherein the panels are sized and arranged in side by side fashion to extend across a fan beam and so that where conjugate rays generated during acquisition always include at least one ray that subtends a detector panel and generates a collected signal even where the other ray in the conjugate pair is directed at a gap between panels, the method further including, after data is acquired, interpolating across each gap and then combining the interpolated data across the gaps with the collected signals to generate back projection data for each of the gap directed rays.

19 Claims, 4 Drawing Sheets

MULTI-PLATE VOLUMETRIC CT SCANNER GAP COMPENSATION METHOD AND APPARATUS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The field of the invention is CT scanners and more specifically volumetric CT scanners that facilitate rapid collection of data required for CT imaging.

Many different types of medical imaging systems have been developed that are used for different purposes. Perhaps the most common type of imaging system category includes X-ray systems wherein radiation is directed across a portion of a patient to be imaged and toward a detector panel. An exemplary X-ray detector panel includes a CsI scintillator coupled with an amorphous silicon array. With radiation directed toward a region of a patient to be images (i.e., a region of interest), the region of interest blocks some of the radiation and some of the radiation passes through the region and is collected by the panel. The amount of radiation that passes through the region along the trajectory of a given radiation ray depends upon the type of tissue along the trajectory. Thus, a tumor may block more radiation than flesh and bone may block more radiation than a tumor and so on. Hence X-ray system can be used to collect a "projection" through a patient. The aforementioned detector panels are generally referred to hereinafter as digital detector panels.

Another imaging system type is generally referred to as a computerized tomography (CT) system. An exemplary CT system includes a radiation point source and a radiation detector mounted on opposite sides of an imaging area. The point source generates radiation that is collimated into a fan beam including a plurality of radiation rays directed along trajectories generally across the imaging area. A region of interest is positioned within the imaging area. With the radiation source turned on the region of interest blocks some of the radiation and some of the radiation passes through the region and is collected by the detector. As in X-ray systems, the amount of radiation that passes through the region of interest along the trajectory of a given radiation ray is dependent upon the type of tissue along the trajectory.

In CT systems the source and detector are rotated about the region of interest so that radiation "projections" through the region can be collected for a large number of angles about the region. By combining the projections corresponding to a volume through the region of interest using a filtering and back projecting technique, a three-dimensional tomographic image of the region volume is generated.

Several factors have to be considered when determining the best way to configure a CT imaging system including relative system costs and resulting image quality.

Referring to FIG. 2, an exemplary CT source 14 and detector 18 are illustrated as being positioned on opposite sides of an imaging area 21. The source 14 is collimated to form beam 16 having a plurality of rays (not separately numbered). For a typical human torso 22 exam a 50 cm field-of-view (FOV) is required. In any CT system the geometry of the system causes a magnification factor (defined as the ratio of the source to detector distance over the source to isocenter (ISO) 24 distance) such that the dimension of the detector array 18 across the fan beam must be greater than the FOV at the region of interest position. In an exemplary CT system the magnification factor is approximately 1.7 so that the minimum detector panel width is 85 cm as illustrated.

One way to construct CT detectors is to configure a large number of CT detector elements (not separately numbered) in an arc about the radiation source 14 as illustrated in FIG. 2. An exemplary detector 18 may include as many as 8 rows of elements perpendicular to a translation or Z-axis where each row may include several hundred elements along the fan beam width (i.e., along the 85 cm width as illustrated in FIG. 2). In addition to the detector elements themselves acquisition circuitry is provided for each detector element for changing an element generated signal into a digital signal for processing. Advantageously such elements can be constructed and configured such that essentially no gap exists between adjacent elements and therefore data that can be used to generate diagnostically useful images can easily be collected.

One problem with CT detectors constructed as described above is that the overall configurations are extremely expensive due to the number of elements and corresponding acquisition circuitry. In addition the structure that maintains element positions with respect to the source is often relatively complex.

One solution to overcoming the problems associated with detectors requiring huge numbers of detector elements and corresponding acquisition circuitry is to provide a single silicon wafer based detector like the digital detectors described above. Thus, one digital detector having a width of 85 cm could be used to collect all CT acquisition data thereby avoiding the expense of separate elements and acquisition circuits.

While digital detectors are extremely useful, unfortunately the silicon wafers or panels required to construct such detectors are only mass produced with relatively small length and width dimensions. The wafer dimensions dictate the size of the detector and hence the FOV. Thus, there is no mass produced digital detector panel that has a width of 85 cm. While large silicon wafers could be produced for such panels ability to achieve consistent manufacturing quality of such large wafers is questionable and cost associated with such an effort is prohibitive.

One solution is to configure a detector panel that collects data across less than an entire FOV and rotate the source and panel through more than 180 degrees about the region of interest. For example, a detector panel having a width dimension slightly greater than one half the full FOV may be configured. For such a panel 360 degrees of rotation would be required to collect data to produce an artifact free image.

While a half FOV panel would be less expensive than a full FOV panel, again, such panels are relatively large, cannot be configured using mass produced silicon wafers and hence are still relatively expensive.

BRIEF SUMMARY OF THE INVENTION

An exemplary embodiment of the invention includes an apparatus including a large CT detector comprised of a plurality of smaller digital detector panels wherein the panels are sized and arranged in side by side fashion to extend across a fan beam and so that conjugate rays generated during data acquisition always include at least one ray that subtends a detector panel and generates a collected signal even where the other ray in the conjugate pair is directed at a gap between panels.

The invention also includes a method to be used with the aforementioned detector, the method including, after data is acquired, interpolating across each gap to generate a modified data set and then combining the modified data set including the data interpolated across the gaps with collected signals corresponding to rays that are conjugates of the rays directed at the gaps to generate back projection data for each of the gap directed rays.

These and other aspects of the invention will become apparent from the following description. In the description, reference is made to the accompanying drawings which form a part hereof, and in which there is shown a preferred embodiment of the invention. Such embodiment does not necessarily represent the full scope of the invention and reference is made therefor, to the claims herein for interpreting the scope of the invention.

DETAILED DESCRIPTION OF THE INVETION

Figure 1:
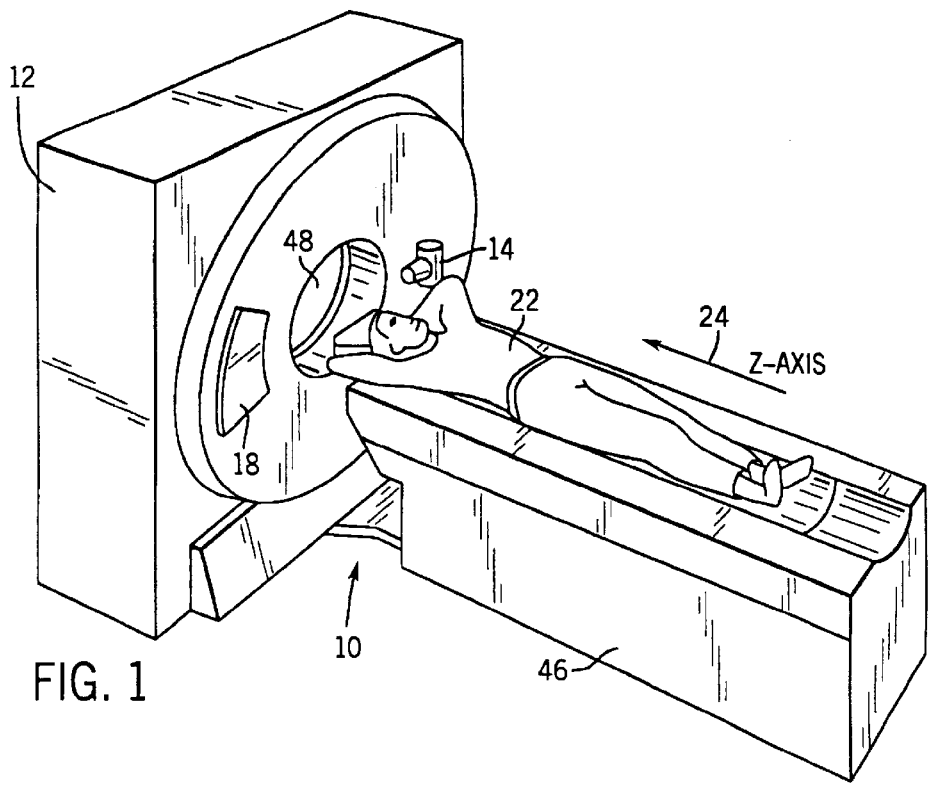
FIG. 1 is a is a perspective view of a CT imaging system.
Figure 2:
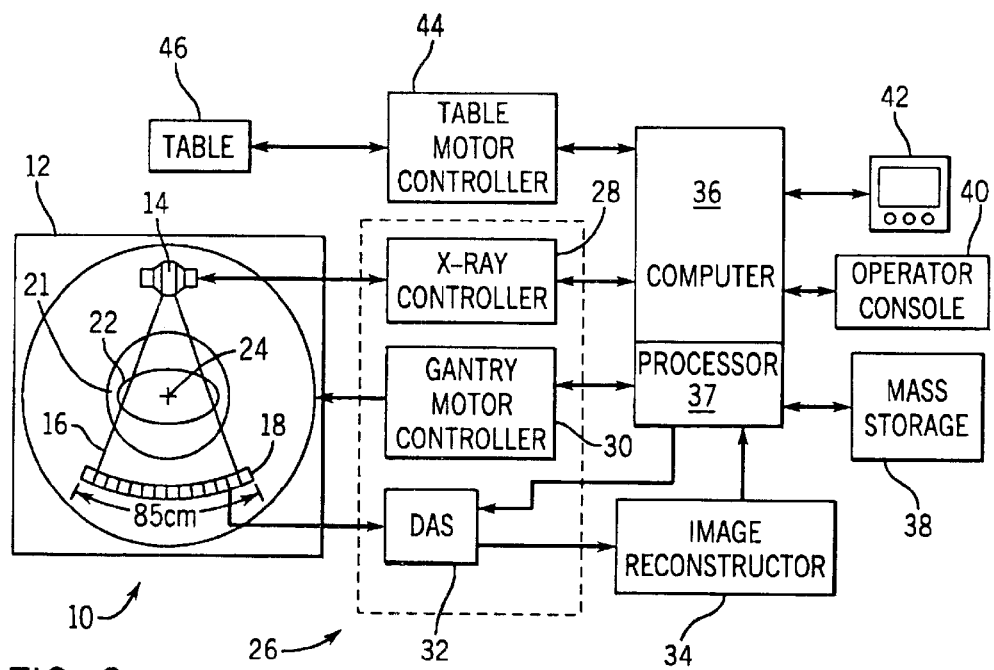
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by a plurality of X-ray panels 20 that together sense the projected x-rays that pass through an object or region of interest 22, for example a region of a patient. During a scan to acquire x-ray projection data, gantry 12 and the components mounted thereon rotate about a center of rotation or isocenter 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector panels 20, determines where across the face of each panel an X-ray was detected and converts the detection positions to digital CT signals that are stored as CT counts in a mass storage device 38 for subsequent processing. Either during data acquisition or thereafter an image reconstructor 34 receives sampled and digitized x-ray data from DAS 32 or retrieves the data from storage device 38 and performs high-speed image processing as described in more detail below to generate one or more images. The images are provided to computer 36 which stores the image on mass storage device 38 for subsequent examination.

Computer 36 also receives commands and scanning parameters from an operator via console 40 that has a keyboard. An associated display 42 allows the operator to observe the images and other data from computer 36. The operator supplied commands and parameters are used by computer 36 to provide control signals and information to DAS 32, x-ray controller 28 and gantry motor controller 30. In addition, computer 36 operates a table motor controller 44 that controls a motorized table 46 to position patient 22 along the Z-axis 15 within gantry 12. Thus, table 46 moves portions of patient 22 through gantry opening 48 along axis 15.

Figure 3:
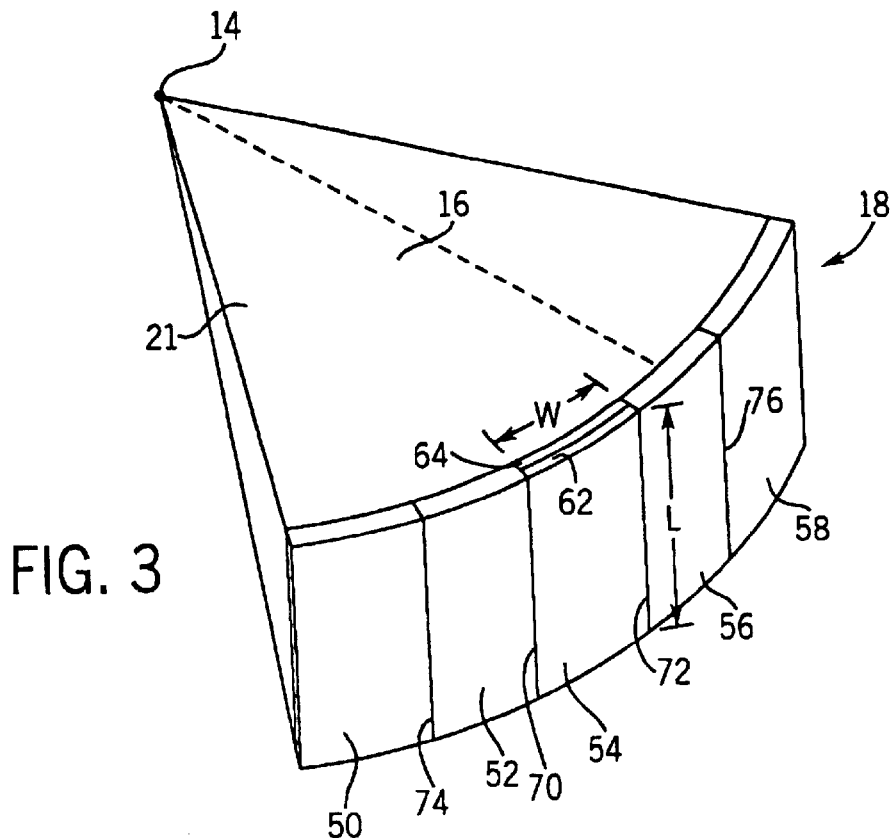
FIG. 3 is a schematic view illustrating a panel based detector array.
Figure 4:
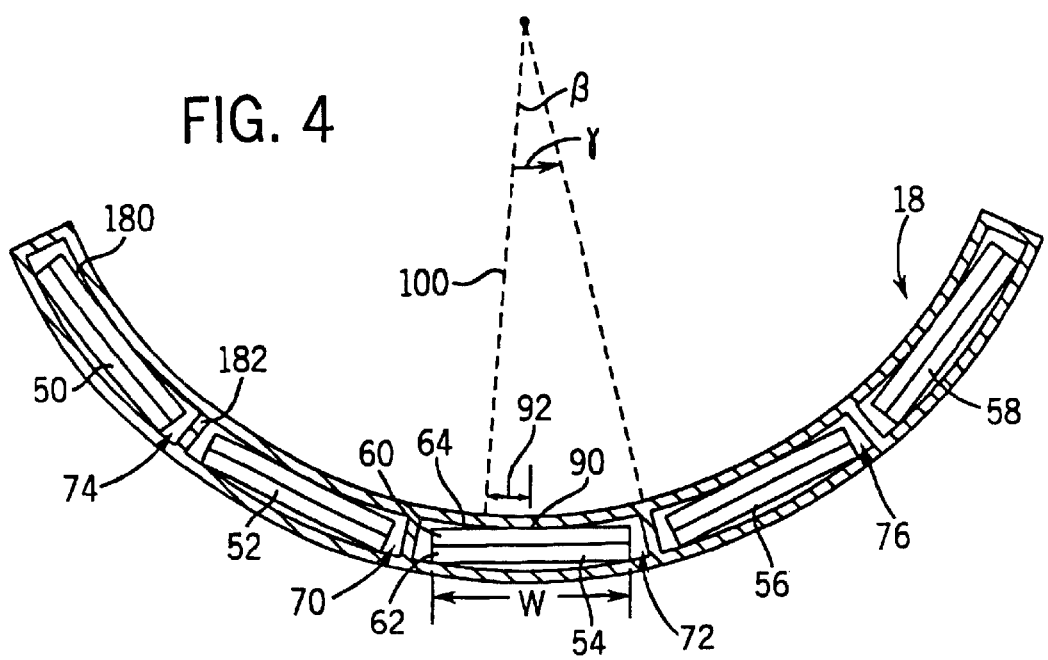
FIG. 4 is a top perspective view of the array of FIG. 3.

Referring to FIGS. 2, 3 and 4, an exemplary detector array 18 according to the present invention is illustrated. Detector array 18 includes a plurality of X-ray or digital detector type panels 50, 52, 54, 56 and 58. All of panels 50 through 58 are similarly constructed and therefore, in the interest of brevity, only central panel 54 will be described here in some detail. With that said, construction and operation of panels like panel 54 are well known in the CT art and therefore will not be explained here in detail.

It should suffice to say that in one embodiment panel 54 includes a CsI scintillator 60 coupled with an amorphous silicon array 62. Crystal 60 defines an essentially flat impact surface 64 having a width dimension W and a length dimension L. When an X-ray impacts surface 64, crystal 60 "scintillates" and generates light that is detected by array 62. Absorbing the light, array 62 generates signals that can be used to determine the energy of the absorbed X-ray and also to determine the exact location along surface 64 at which the X-ray impacted. Panel 54 also includes acquisition circuitry (not illustrated) linked to array 62 and receiving signals therefrom that identifies both the energy associated with a detected X-ray and the X-ray impact point. The energy and impact point of each X-ray is provided to computer 36 for processing and storage. To this end computer 36 includes a processor 37 for data processing and system management.

Referring still to FIGS. 2, 3 and 4, panels 50, 52, 54, 56 and 58 are arranged in side by side fashion such that their width dimensions W line up along the fan beam 16. Thus, instead of each panel (e.g., 54) and corresponding silicon array (e.g., 62) having to stretch across the entire 85 cm FOV or even one half the FOV, each width dimension W need only extend across a small portion of the FOV. For instance, in FIG. 3, assuming an 85 cm FOV requirement and five panels as illustrated, each panel width dimension would only have to be approximately 17 cm. In other embodiments where less or more panels are employed the panel width dimensions W would be adjusted up or down accordingly. The required length dimension L is relatively small. Thus, with the inventive configuration the length L and width W dimensions are relatively small and therefore the 85 cm FOV or even larger FOVs are easy to accommodate using standard and mass produced digital detector panels with silicon wafers 62.

While the configuration illustrated in FIGS. 3 and 4 overcomes the FOV problems discussed above, mass-produced digital detector panels like panel 54 have been configured only to accommodate their own FOV and not to be arranged adjacent other similar panels to accommodate larger FOVs. For this reason some panel hardware (e.g., panel sealing components, read out leads for acquisition circuitry, etc.) extends laterally beyond length L and width W dimensions. For this reason, even when panels 50, 52, 54, 56 and 58 are positioned as close as possible to form array 18, a finite gap will exists between each two adjacent panels. For example, in FIGS. 3 and 4 gaps between adjacent panels are identified by numerals 70, 72, 74 and 76.

From a tomographic reconstruction point of view gaps between panels and thus uncollected projection samples are highly undesirable and can easily lead to image artifacts that appreciably reduce the diagnostic usefulness of resulting images. For example, referring to FIG. 5, an image of a rib phantom generated with a conventional CT imaging system including a large number of CT detector elements arranged to form a detector array is illustrated. The FIG. 5 image was formed without simulating gaps and therefore image is relatively good.

Figure 5:
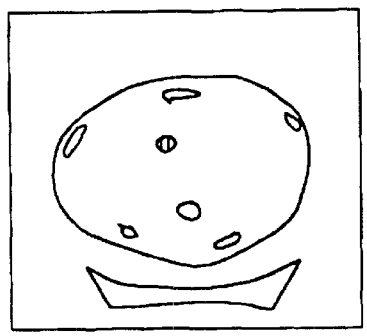
FIG. 5 is an exemplary rib phantom image.
Figure 6:
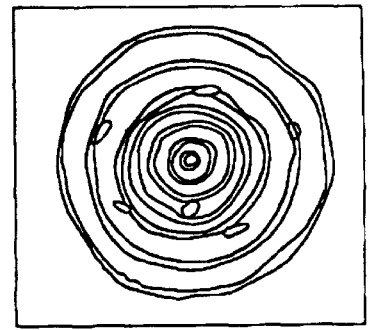
FIG. 6 is an exemplary rib phantom image similar to the image of FIG. 5, albeit without the benefits of least one embodiment of the present invention.

Referring also to FIG. 6 a rib phantom image is illustrated that was generated using the same conventional CT system that generated the FIG. 5 image, but with gap simulation. To simulate gaps (e.g., 70 in FIGS. 3 and 4) some of the detector element readings corresponding to the locations of gaps in a panel-based system were set to zero in the conventional detector array. In FIG. 5 nine mm gaps were simulated with the gaps separated by 100 mm. Note that the 9 mm simulated gap size is much larger than a gap that would likely occur in a panel-based detector. The excessive gap was chosen to show the robustness of the present invention and also to clearly illustrate the problems associated with a system that does not employ the present invention.

The gaps were simulated such that the spaces between the gaps where symmetrically arranged about the radiation source. For example, center detectors that comprised the 100 mm in the center of the array where arranged so that a central fan beam ray subtended the middle of the center detectors. Moving out from the middle of the center detectors in either direction gaps where symmetrically arranged about the center detectors. Clearly the FIG. 6 image includes several image artifacts, in particular round circles, that result directly from the simulated gaps and that minimize the diagnostic usefulness of the resulting image.

As well known in the CT industry, if data is collected through 360 degrees of rotation, the acquired data potentially includes two data samples and resulting data signals for each beam trajectory through the region of interest, one sample or signal corresponding to a ray along a first trajectory direction and another sample or signal corresponding to a ray along a second trajectory direction opposite the first. The oppositely directed rays are referred to generally as conjugate rays. Thus, one solution to overcome the artifact problems associated with gaps would seem to be to supplement samples or signals that were un-collected due to gaps with collected samples or signals corresponding to conjugate rays.

The present inventors have recognized that one problem with panel-based arrays is that, when the panels are configured in certain ways, when a first of a conjugate ray pair is directed toward a gap during data acquisition the second ray of the conjugate ray pair is also directed at a gap so that neither of the conjugate rays is detected during acquisition. For this reason, where such configurations are constructed, conjugate supplementation is essentially impossible. As it turns out, one group of configurations that result in both rays of a conjugate pair being directed toward gaps includes all panel configurations where the gaps are symmetrically arranged about the center of the detector array as simulated to generate the image of FIG. 6.

Thus, one concept developed by the present inventors is to offset the detector panels 50–58 such that at least one of each pair of conjugate rays subtends a panel impact surface and is detected thereby generating a collected data signal that can be used for conjugate supplementation of the conjugate un-collected signal. In effect the offset results in "incomplete conjugate sample pairs" including one collected data signal and one un-collected signal instead of two un-collected signals.

To this end, referring still to FIG. 4, mid-point 90 along width dimension W bisects panel 54 and ray 100 is a central beam ray that passes through isocentric point 24. As illustrated, panel 54 has been shifted to the right an offset distance 92 with respect to ray 100. Any of several different distances 92 can be selected with the one limitation that the shift must result in placement of gaps (e.g., 70 and 72) such that when a first ray subtends a gap, the first ray's conjugate will not subtend a gap and an incomplete conjugate sample pair results.

In addition, although more difficult to perceive in the illustration, the relative positions of each of lateral panels 50, 52, 56 and 58 have also been modified in two ways. First, each of the panels have been shifted to the right to accommodate the central panel shift 92 and maintain small gaps 70 and 72. Second, in order to maintain the panels essentially the same distance from source 14, the angles of each of the lateral panels have been changed slightly so that the array 18 forms an arc about source 14.

While each of panels 50–58 is illustrated as having an identical width W, it is contemplated that in some embodiments the panels may have different widths. For example, because array 18 is generally shifted to the right a distance 92, the overall dimension of array 18 to the right of central ray 100 would be greater than the overall dimension of array 18 to the left of central ray 100. To maintain symmetry between overall dimensions on either side of ray 100 despite the shift, one or more of the panels (e.g., 50 or 52) to the left of ray 100 may have a greater width dimension W than one or more of the panels (e.g. 56 or 58) to the right of ray 100.

In addition, panel widths W may also be selected to ensure that at least one of each conjugate ray pair does not fall within a gap but rather subtends a panel impact surface 64. Thus, it has been recognized that even the central panel shift and corresponding repositioning of lateral panels described above may not result in a panel configuration that produces at least one collected signal for each conjugate ray pair and that positioning of each gap must be considered in conjunction with positioning of each other gap to ensure the desired result (i.e., at least one collected sample for each conjugate pair). Hence, if widths of panels 50–58 are sized such that both rays of any conjugate pair subtend gaps one or more of the panel widths W can be altered during the array design stage to avoid this problem.

In essence, the design methodology calls for selecting panel sizes and configuring the panels such that the gap location trajectories interleave each other so that the acquired data includes conjugate sample pairs and incomplete pairs (i.e., including at least one collected signal) and so that there are no conjugate pairs for which no signals are collected.

Referring still to FIG. 4 a radio-translucent sealing cover 180 is illustrated that essentially seals all panels 50–58. Covers like 180 are required for silicon type detector panels. By providing a single sealing cover 180 for all panels the gaps between panels can be minimized. In the alternative, each panel 50–58 may be separately sealed (see 182 in FIG. 4). While this sealing option increases gap size it results in a more serviceable system where separate panels can be serviced without disturbing the entire detector array 18.

One other aspect of the present invention is a process whereby the signals collected using the inventive array configuration are processed to generate a high quality and diagnostically useful image. To this end the data processing steps in one embodiment include interpolation, weighting and then known filtering and back projecting techniques.

First, where a gap results in un-collected signals, the data or signals corresponding to rays adjacent the gap are interpolated across the gap. To this end rays adjacent a gap are referred to as proximate rays and signals generated by those rays subtending edges of the panels are referred to as proximate signals. To preserve high-frequency information contents in the projection, in one embodiment a high order interpolation scheme such as the LaGrange interpolator, is employed. The region over which interpolation is performed is a matter of designer choice.

Interpolation is required as, without interpolation, the weights assigned to the projection samples corresponding to the gaps would have to be zero which would adversely affect the weighting process and the quality of the final image. Specifically, if gaps are assigned zero contribution a transition region on either side of each gap that has to be weighted would be appreciably increased which in turn would cause increased noise in the final image. The interpolation process results in a modified data set including the collected signals corresponding to rays that subtended panels and the interpolated signals corresponding to the gaps.

After interpolation the resulting interpolated signals and "conjugate collected signals" (i.e., where an interpolated signal is associated with a specific ray trajectory that is a first ray in a conjugate pair, the conjugate collected signal in the signal corresponding to the second ray in the conjugate pair) are weighted thereby generating data for filtering and back projection purposes. To ensure artifact-free reconstruction, in one embodiment the weighting function satisfies the following two conditions. First, the weighting function has to be continuous and differentiable within the finite dimension across the gap (i.e., along the fan angle $\gamma$). Second, the weights for conjugate samples or signals must sum up to unity.

Figure 7:
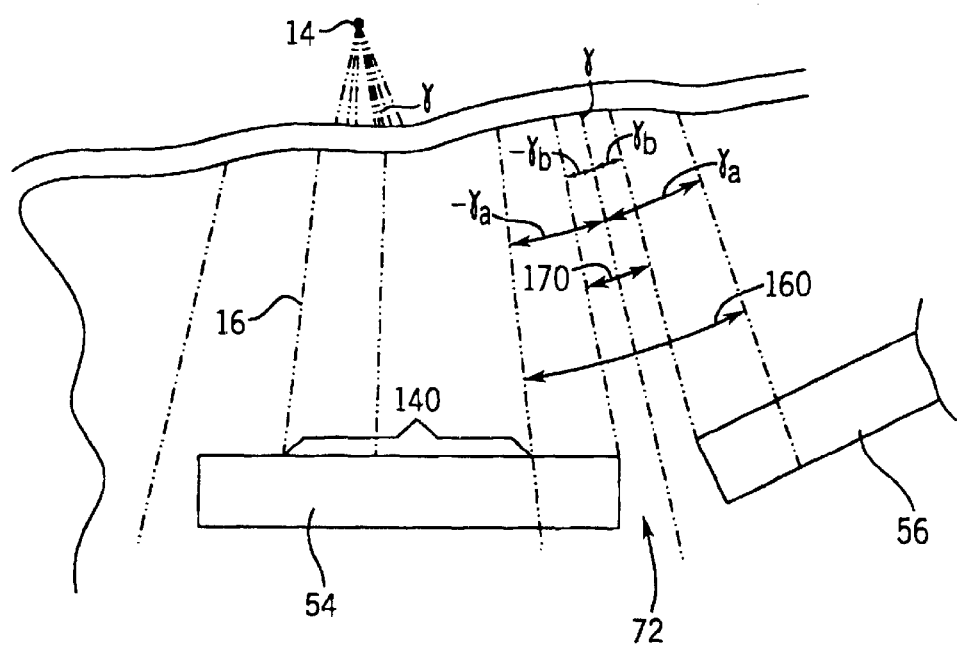
FIG. 7 is similar to FIG. 4, albeit illustrating a smaller portion of the array illustrated in FIG. 4.

Referring to FIG. 7 two panels 54 and 56 are illustrated in an enlarged view to useful in understanding the geometry of exemplary gap 72 for the purpose of defining a transition region and a window function $\Gamma$ for the weighting process. In FIG. 7, the center of nth gap 72 is identified by fan angle $\gamma_n$ and the transition region 160 there around extends in both directions past the edges of gap 72 and partially into adjacent detector panels 54 and 56. The transition region 160 is the area between $-\gamma_a$ and $\gamma_a$. A sub-region 170 within transition region 160 defines the space between adjacent panels 54 and 56 and is between $-\gamma_b$ and $\gamma_b$. $\gamma_a$ and $\gamma_b$ define weighting regions for each gap. With the transition and sub-regions 160, 170, respectively, so defined, a useful window function $\Gamma$ can be defined as:

$$\Gamma(\gamma) = 3\theta^2(\gamma) - 2\theta^3(\gamma)$$

$$\theta(\gamma) = \begin{cases} \dfrac{\gamma + \gamma_a}{\gamma_a - \gamma_b} & -\gamma_a \leq \gamma < \gamma_b \\ 1 & -\gamma_b \leq \gamma < \gamma_b \\ \dfrac{\gamma_a - \gamma}{\gamma_a - \gamma_b} & \gamma_b \leq \gamma < \gamma_a \\ 0 & \text{otherwise} \end{cases} \quad \text{Eq. 1}$$

With the window so defined, in one embodiment the weighting function can be described by the following equation:

$$w(\gamma, \beta, z) = 1 - \xi \sum_{n=1}^{N} \Gamma(\gamma - \gamma_n) + \xi \sum_{n=1}^{N} \Gamma(\gamma + \gamma_n) \quad \text{Eq. 2}$$

Where N is the number of gaps present in the detector array, $\gamma_n$ is the center of the gap, $\xi$ is a parameter that controls the amount of contribution of the interpolated projection samples to the final image, z is the location of a detection along axis 24 and $\beta$ is the angle defined by the central fan beam 100.

Referring again to FIG. 7, it should be appreciated that while the general concept behind placement of the panels (e.g., 54, 56) is to make sure that at least one of each conjugate ray pair subtends a detector as opposed to passing through a gap, because the transition region is wider than the width of a gap, in at least one embodiment of the invention the panels are placed and arranged such that at least one of each conjugate ray pair of rays subtends a non-transition region detector section. Thus, for example, in FIG. 7 the right end of panel 54 is within the transition region corresponding to gap 72. Likewise, the left end of panel 54 is within the transition region corresponding to gap 70. The space 140 between the panel ends that is not in any transition region comprises the non-transition region detector or panel section. Similarly ends of each of the other panels are within transition regions corresponding to adjacent gaps and the panel sections there between are non-transition sections. According to this embodiment the panels should be arranged such that, where one of a pair of conjugate rays is directed toward one of the gaps, the other ray of the pair subtends a non-transition region panel section (e.g., 140).

Experimental results have shown that by employing panels arranged in accordance with the above teachings significant improvement in artifact reductions is observed. Where realistic gap sizes (e.g., 1 mm) were simulated essentially no artifacts were observed. The resulting image where 9 mm gaps were simulated is essentially as shown in FIG. 5.

Figure 8:
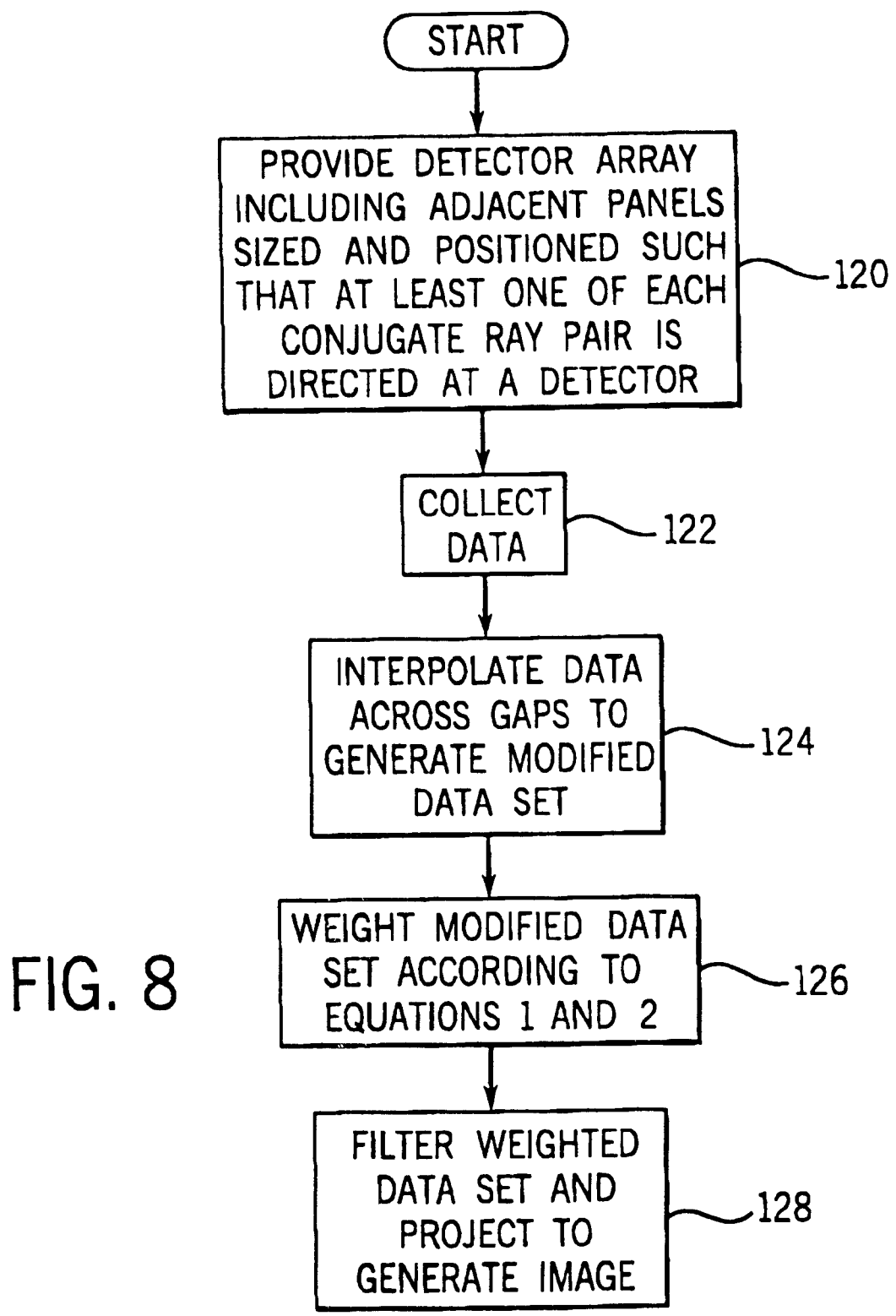
FIG. 8 is a flow chart illustrating a method according to one embodiment of the invention.

Referring now to FIG. 8 an exemplary process according to the present invention is illustrated. Beginning at process block 120 a detector array is provided that includes laterally stacked adjacent x-ray panels where the panels are arranged and sized such that gaps between each two adjacent panels are positioned so that at least one ray of each conjugate ray pair that is detected during data acquisition subtends a portion of a detector panel that is outside a transition region. Next, referring also to FIG. 1, with a region of interest (i.e. the region of a patient that is to be detected) positioned within gantry 12 and between source 14 and detector 18, source 14 is turned on so that detector 18 begins to collect data and source 14 and detector 18 are rotated about the gantry 12 to collect data for $2\pi$ rotations (i.e. 360°) about the region of interest.

After data has been collected for $2\pi$ rotations, referring also to FIG. 2, a processor within computer 36 interpolates across each of the gaps (e.g., 70). Continuing, at block 126, processor 27 applies the weighting function that is described by Equations 1 and 2 above to generate estimated signals for each of the gap directed rays. At block 128 the processor filters and backprojects the weighted data to generate an image that can be viewed via display 42.

It should be understood that the methods and apparatuses described above are only exemplary and do not limit the scope of the invention, and that various modifications could be made by those skilled in the art that would fall under the scope of the invention. For example, while the embodiment described above teaches data processing including interpolation and weighting, it has been found that where gaps between panels are extremely small, interpolation alone can produce diagnostic quality images without requiring the weighting process. Also, in this regard, where the gaps are small so that only interpolation and no weighting is required, data need only be collected during π+2γ degrees as the conjugate rays are not required for weighting purposes. For instance, where the gaps are 1 mm the resulting images were of relatively high quality even without weighting the interpolated data.

In addition, while not illustrated above it is known in the art that X-ray detectors like panel 54 have to be sealed in some fashion. The invention contemplates configurations where each panel in array 18 is sealed separately or other configurations where all panels are sealed within a single sealing member.

Moreover, while array 18 is illustrated as being flat some systems include flat arrays. The inventive concepts could clearly be applied to flat array configurations.

In addition, while one division of a transition region and a sub-region are illustrated in FIG. 7, other divisions are contemplated where the sub-region may be larger or smaller or the transition region may be larger or smaller.

Furthermore, any interpolation function or weighting function could be used with the present invention.

To apprise the public of the scope of this invention, the following claims are made:

What is claimed is:

1. A CT detector apparatus for use with a radiation source that generates a radiation fan beam having a width and a thickness, the apparatus for collecting beam ray intensity signals and comprising:
   at least first and second digital detector panels, each detector panel having a panel width and a panel length, the panels juxtaposed in a side-by-side arrangement to form a panel array wherein each panel length extends essentially across the entire detection area thickness and the combined panel widths extend essentially across the entire detection area width.

2. A CT detector apparatus for use with a radiation source that generates a radiation fan beam having a width and a thickness, the apparatus for collecting beam ray intensity signals and comprising:
   at least first and second digital detector panels, each detector panel having a panel width and a panel length, the panels juxtaposed in a side-by-side arrangement to form a panel array wherein each panel length extends essentially across the entire detection area thickness and the combined panel widths extend essentially across the entire detection area width;
   wherein the fan beam includes a central ray and a plurality of lateral rays defining fan angles on both sides of the central ray, the central ray defining a fan beam projection angle and wherein during acquisition each of the source and array are rotated about an imaging area to collect signals from a plurality of projection angles, each projection angle and fan angle defining a ray trajectory through the imaging area, during acquisition a conjugate pair including first and second oppositely directed rays are directed along each trajectory, the first and second panels forming a gap there between, a transition region including at least the area of the gap, at least some rays directed toward the transition region, the panels arranged such that, for each conjugate pair, if the first ray is directed toward the transition region, the second ray subtends a non-transition region panel section and the resulting signals for the trajectory comprise an incomplete conjugate signal pair.

3. The apparatus of claim 2 further including additional panels arranged adjacent the first and second panels where each two adjacent panels form a gap there between such that a separate transition region corresponding to each gap includes the gap, during acquisition, at least some of the rays directed at each transition region, the panels arranged such that, for each conjugate pair, if the first ray is directed at a transition region the second ray subtends a non-transition region panel section and the resulting signals for the trajectory comprise an incomplete conjugate signal pair.

4. The apparatus of claim 3 wherein one of the panels is a central panel and the central ray subtends the central panel, the central panel includes a midpoint that bisects the panel width and the central ray is offset from the midpoint.

5. The apparatus of claim 4 wherein the panels are arranged to form an arc about the source.

6. The apparatus of claim 3 wherein rays proximate a gap are proximate rays that generate proximate signals and, wherein, the apparatus further includes a processor that interpolates the proximate signals across the gap to generate a modified data set including the interpolated signals and collected signals.

7. The apparatus of claim 6 wherein the signal corresponding to the second ray is a collected signal and the apparatus further includes a processor that, for each incomplete pair, generates an estimated signal for the first ray that is a function of at least the collected signal and an interpolated signal corresponding to the first ray.

8. The apparatus of claim 7 wherein, after interpolating, the processor weights the interpolated signals and the collected signals to produce the estimated signals.

9. The apparatus of claim 8 wherein the processor weights the modified data set and collected signals by solving the following equation:

$$w(\gamma, \beta, z) = 1 - \xi \sum_{n=1}^{N} \Gamma(\gamma - \gamma_n) + \xi \sum_{n=1}^{N} \Gamma(\gamma + \gamma_n)$$

where N is the number of gaps present in the detector array, $\gamma_n$ is the center of a gap, $\zeta$ is a parameter that controls the amount of contribution of the interpolated signals to the final image, z is the location of a detection along a system translation axis, $\beta$ is the angle defined by the central fan beam and $\Gamma$ is a window function defined by the equation:

$$\Gamma(\gamma) = 3\theta^2(\gamma) - 2\theta^3(\gamma)$$

where:

$$\theta(\gamma) = \begin{cases} \dfrac{\gamma + \gamma_a}{\gamma_a - \gamma_b} & -\gamma_a \leq \gamma < \gamma_b \\ 1 & -\gamma_b \leq \gamma < \gamma_b \\ \dfrac{\gamma_a - \gamma}{\gamma_a - \gamma_b} & \gamma_b \leq \gamma < \gamma_a \\ 0 & \text{otherwise} \end{cases}$$

where $\gamma_a$ and $\gamma_b$ define weighting regions for each gap.

10. A CT detector apparatus for use with a radiation source that generates a radiation fan beam having a width and a thickness, the apparatus for collecting beam ray intensity signals and comprising:
   at least first and second digital detector panels, each detector panel having a panel width and a panel length, the panels juxtaposed in a side-by-side arrangement to form a panel array wherein each panel length extends essentially across the entire detection area thickness and the combined panel widths extend essentially across the entire detection area width;

wherein each panel includes an amorphous silicon panel.

11. A CT detector apparatus for use with a radiation source that generates a radiation fan beam having a width and a thickness, the apparatus for collecting beam ray intensity signals and comprising:

at least first and second digital detector panels, each detector panel having a panel width and a panel length, the panels juxtaposed in a side-by-side arrangement to form a panel array wherein each panel length extends essentially across the entire detection area thickness and the combined panel widths extend essentially across the entire detection area width;

wherein a radio translucent sealing cover is provided that encloses the entire array.

12. A CT detector apparatus for use with a radiation source that generates a radiation fan beam having a width and a thickness, the apparatus for collecting beam ray intensity signals and comprising:

at least first and second digital detector panels, each detector panel having a panel width and a panel length, the panels juxtaposed in a side-by-side arrangement to form a panel array wherein each panel length extends essentially across the entire detection area thickness and the combined panel widths extend essentially across the entire detection area width;

wherein a separate radio translucent sealing cover is provided for each of the detector panels.

13. A method for use with a system including a radiation source and a detector array, the array including at least first and second digital detector panels, each detector panel having a panel width and a panel length, the panels juxtaposed in a side-by-side arrangement to form a panel array with gaps between each two adjacent panels, the source generating a radiation fan beam having a width and a thickness, each panel length extending essentially across the entire detection area thickness and the combined panel widths extend essentially across the entire detection area width, the beam including a central ray and a plurality of lateral rays defining fan angles on both sides of the central ray, the central ray defining a fan beam projection angle and wherein during data acquisition each of the source and array are rotated about an imaging area to collect ray intensity signals from a plurality of projection angles, each projection angle and fan angle defining a ray trajectory through the imaging area, during data acquisition conjugate ray pairs including first and second oppositely directed rays directed along each ray trajectory, each two adjacent panels forming a gap there between such that during data acquisition no data is collected for ray trajectories between the source and each of the gaps, the method comprising the steps of:

arranging the panels such that, for each ray trajectory, if the first ray is directed toward a gap, the second ray subtends a panel and the resulting signals for the trajectory comprise an incomplete conjugate signal pair including a collected signal; and after data acquisition, for each incomplete pair, using the collected signal to generate an estimated signal for the second ray.

14. The method of claim 13 wherein, for each incomplete pair, each first ray corresponding to an un-collected signal and rays proximate the gap are proximate rays and generate proximate signals and, wherein, the method further including the step of interpolating the proximate signals across the gap to generate a modified data set including interpolated signals for each ray directed toward the gap and collected signals.

15. The method of claim 14 wherein the step of using includes the step of weighting the interpolated signals and the collected signals to produce the estimated signals.

16. The method of claim 15 wherein the weighting step includes weighting by solving the following equation:

$$w(\gamma, \beta, z) = 1 - \xi \sum_{n=1}^{N} \Gamma(\gamma - \gamma_n) + \xi \sum_{n=1}^{N} \Gamma(\gamma + \gamma_n)$$

where N is the number of gaps present in the detector array, $\gamma_n$ is the center of a gap, $\zeta$ is a parameter that controls the amount of contribution of the interpolated signals to the final image, z is the location of a detection along a system translation axis, $\beta$ is the angle defined by the central fan beam and $\Gamma$ is a window function defined by the equation:

$$\Gamma(\gamma) = 3\theta^2(\gamma) - 2\theta^3(\gamma)$$

where:

$$\theta(\gamma) = \begin{cases} \dfrac{\gamma + \gamma_a}{\gamma_a - \gamma_b} & -\gamma_a \le \gamma < \gamma_b \\ 1 & -\gamma_b \le \gamma < \gamma_b \\ \dfrac{\gamma_a - \gamma}{\gamma_a - \gamma_b} & \gamma_b \le \gamma < \gamma_a \\ 0 & \text{otherwise} \end{cases}$$

where $\gamma_a$ and $\gamma_b$ define weighting regions for each gap.

17. A CT system comprising:

a supporter;

a radiation source mounted to the supporter for rotation about a rotation axis and an imaging area, the source generating a radiation fan beam having a width and a thickness, the fan beam including a central ray and a plurality of lateral rays defining fan angles on both sides of the central ray, the central ray defining a fan beam projection angle;

at least first and second detector panels, each detector panel having a panel width and a panel length, the panels juxtaposed in a side-by-side arrangement to form a panel array, the array mounted to the supporter opposite the source for rotation about the axis, each panel length extending essentially across the entire detection area thickness and the combined panel widths extending essentially across the entire detection area width, wherein, during acquisition each of the source and array are rotated about the imaging area to collect signals from a plurality of projection angles, each projection angle and fan angle defining a ray trajectory through the imaging area, during data acquisition conjugate ray pairs including oppositely directed first and second rays directed along each ray trajectory, adjacent panels forming a gap there between such that during acquisition no signal is collected for ray trajectories between the source and each of the gaps, the panels arranged such that, for each ray trajectory, if the first ray subtends a gap the second ray subtends a panel and the resulting signals for the trajectory comprise an incomplete conjugate signal pair, for each incomplete pair the signal corresponding to the ray that subtends a panel being a collected signal; and a processor that receives the signals and that, for each incomplete pair, generates an estimated signal for the second ray as a function of at least the collected signals.

18. The apparatus of claim 17 wherein, for each incomplete pair the first ray corresponds to an un-collected signal and rays proximate the gap are proximate rays that generate proximate signals and, wherein, the processor generates by interpolating the proximate signals across the gap to generate a modified data set and then weighting the modified data set to produce the estimated signals.

19. The apparatus of claim 18 wherein the processor weights the modified data set according to the following equation:

$$w(\gamma, \beta, z) = 1 - \xi \sum_{n=1}^{N} \Gamma(\gamma - \gamma_n) + \xi \sum_{n=1}^{N} \Gamma(\gamma + \gamma_n)$$

where N is the number of gaps present in the detector array, $\gamma_n$ is the center of a gap, $\zeta$ is a parameter that controls the amount of contribution of the interpolated signals to the final image, z is the location of a detection along a system translation axis, $\beta$ is the angle defined by the central fan beam and $\Gamma$ is a window function defined by the equation:

$$\Gamma(\gamma) = 3\theta^2(\gamma) - 2\theta^3(\gamma)$$

where:

$$\theta(\gamma) = \begin{cases} \dfrac{\gamma + \gamma_a}{\gamma_a - \gamma_b} & -\gamma_a \leq \gamma < \gamma_b \\ 1 & -\gamma_b \leq \gamma < \gamma_b \\ \dfrac{\gamma_a - \gamma}{\gamma_a - \gamma_b} & \gamma_b \leq \gamma < \gamma_a \\ 0 & \text{otherwise} \end{cases}$$

where $\gamma_a$ and $\gamma_b$ define weighting regions for each gap.

* * * * *